United States Patent [19]

Takayanagi et al.

[11] Patent Number: 4,859,763

[45] Date of Patent: Aug. 22, 1989

[54] PREPARATION PROCESS OF DL-LACTIC ACID-GLYCOLIC ACID-COPOLYMER

[75] Inventors: Hiroshi Takayanagi; Tadashi Kobayashi, both of Omuta; Takayoshi Masuda, Tokai; Hosei Shinoda, Nishikasugai, all of Japan

[73] Assignee: Mitsui Toatsu Chemicals, Incorporated, Tokyo, Japan

[21] Appl. No.: 216,371

[22] Filed: Jul. 8, 1988

[30] Foreign Application Priority Data

Jul. 14, 1987 [JP] Japan ................................. 62-173884
Jul. 1, 1988 [JP] Japan ................................. 63-162396

[51] Int. Cl.$^4$ ............................................. C08G 63/10
[52] U.S. Cl. ..................................... 528/357; 424/426
[58] Field of Search ................................. 528/357, 354

[56] References Cited

U.S. PATENT DOCUMENTS

| | | | |
|---|---|---|---|
| 3,284,417 | 11/1966 | Hostettler et al. | 528/357 |
| 3,442,871 | 5/1969 | Schmitt et al. | 528/357 |
| 3,839,297 | 10/1974 | Wasserman et al. | 528/357 |
| 4,331,652 | 5/1982 | Ludwig et al. | |

FOREIGN PATENT DOCUMENTS 0058481 1/1982 European Pat. Off. .

*Primary Examiner*—Earl Nielsen
*Attorney, Agent, or Firm*—Burns, Doane, Swecker & Mathis

[57] ABSTRACT

A process for copolymerizing lactide and glycolide by using a specific amount of stannous octoate as a catalyst in the presence of a polymerization regulator at temperature of 200°–230° C. to prepare dl-lactic acid-glycolic acid-copolymers which contain 50–60 mol % of a dl-lactic acid unit and 40–50 mol % of a glycolic acid unit and have inherent viscosity of 0.4–0.6 in chloroform.

3 Claims, No Drawings

PREPARATION PROCESS OF DL-LACTIC ACID-GLYCOLIC ACID-COPOLYMER

BACKGROUND OF THE INVENTION:

a. Field of the Invention:

This invention relates to a preparation process of dl-lactic acid-glycolic acid-copolymers used as matrices of molded slow-releasing drugs.

b. Description of the Prior Art:

Polylactic acid, polyglycolic acid and other similar compounds are bioabsorbable and hydrolyzable polymers. By applying these properties, these polymers are used for medical care as sutures or matrices of molded slow-releasing drugs in the form of pellet, film and bar which are administered by such methods as, for example, implanatation.

Particularly polylactic acid has better processing ability and solubility in solvents as compared with polyglycolic acid, and is frequently used as a matrix in the form of various molded drugs. Polylactic acid, however, has a slow rate of decomposition in vivo, and is hence disadvantageous in that polylactic acid remains in the organism as long as one to several months after releasing the drugs.

Therefore, it has also been known recently to use copolymers obtained by copolymerizing lactic acid with glycolic acid.

According to the information of the present inventors in particular, a copolymer containing 50–60 mol % of a lactic acid unit and 40–50 mol % of a glycolic acid unit and also having such physical properties as a weight average molecular weight of 30,000–100,000, good solubility in chloroform and an inherent viscosity of 0.4–0.6 in a 1 g/100 ml solution has suitable absorbability in vivo and solubility. Therefore, it has already been known that the copolymer can be applied for various matrices of drugs in a wide field of medication forms and is particularly suitable for the slow-releasing drugs used for the implantation in the form such as pellet, film and micro capsule.

A low molecular weight lactic acid-glycolic acid-copolymer having a relatively high content of the lactic acid unit like the copolymer of this invention and the process for preparing the same have been disclosed in Japanese Laid-Open Patent Nos. 64824/1987 and 46823/1981.

Japanese Laid-Open Patent No. 64824/1987 discloses a low molecular weight and heterogeneous lactic acid-glycolic acid-copolymer containing 25–100 mol % of the lactic acid unit and 0–75 mol % of the glycolic acid unit, being soluble in benzene and having an intrinsic viscosity of not more than 0.5 in a 1 g/100 ml solution of benzene. It also discloses a similar copolymer containing the same proportion of the above units, being insoluble in benzene and having an intrinsic viscosity of not more than 4 in a 1 g/100 ml solution of chloroform or dioxane.

As an illustrative example of the preparation process, the above patent describes that the desired copolymer is obtained by copolymerizing a lactide with a glycolide at 160° C. in the presence of dl-lactic acid containing water as a polymerization regulator by the use of stannous octoate as a catalyst in an amount of 0.2 wt. % based on the sum of the lactide and the glycolide.

In addition, Japanese Laid-Open Patent No. 46823/1981 discloses a lactic acid/glycolic acid-copolymer used for a matrix of molded slow-releasing drugs containing parasitic ascaricide and the process for preparing the same.

This patent describes that a lactic acid-glycolic acid-copolymer being derived from about 70–80 wt. % of lactic acid and about 30–20 wt. % of glycolic acid and having such desired properties as an inherent viscosity of about 0.13–0.23 in a chloroform solution and a weight average molecular weight of about 15,000–30,000 is obtained by conducting the copolymerization in the presence of a strongly acidic ion exchange resin.

As stated above in Japanese Laid-Open Patent No. 64824/1987, the copolymer having the desired properties is obtained by using stannous octoate in an amount of about 0.2 wt. % based on the sum of lactic acid and glycolic acid. However, the tin content in the molded drugs administered in vivo must, of course, be minimized.

On the other hand, it is difficult to remove tin metal from the copolymer obtained. Although stannous octoate is known to have a remarkable effect as the catalyst, stannous octoate contains a metallic tin ingredient of 28–30 wt. %. Therefore, the amount used as described in the patent inevitably causes residue of tin metal in an amount of several hundred ppm and is expected to have adverse effects to some extent.

As a result, the above Japanese Laid-Open Patent No. 46823/1981 is though to have carried out the copolymerization of lactic acid with glycolic acid by using the strongly acidic ion exchange resin in the absolute absence of the metallic catalyst.

Besides the slow-releasing drugs, no endotoxin must be contained in materials administered in vivo.

Endotoxin is lipopolysaccharides existing in cell walls of the bacteria and known to exert biological activities such as decrement in leucocytes and blood platelets, fever, hemorrhagic necrosis of bone marrow and reduction in flood sugar value.

The above Japanese Laid-Open Patent No. 64824/1987 illustrates an example for conducting the copolymerization at 160° C. Polymerization at such a temperature causes a problem in the resultant polymer which enhances the possibility of containing residual endotoxin derived from monomers and other raw materials.

SUMMARY OF THE INVENTION

The object of this invention is to provide a preparation process of a dl-lactic acid-glycolic acid-copolymer which is harmless to mankind and has a specific range of properties.

The above object of this invention can be achieved by the following process:

A preparation process, from a lactide and a glycolide, of a dl-lactic acid-glycolic acid-copolymer containing 50–60 mol % of the lactic acid unit and 40–50 mol % of the glycolic acid unit and having an inherent viscosity of 0.4–0.6 in chloroform which comprises conducting the copolymerization at a temperature of 200°–230° C. in the presence of a polymerization regulator, and by using stannous octoate as a catalyst in an amount of 0.005–0.015 wt. % based on the sum of the lactide and the glycolide.

The present inventors have intensively carried out the investigation with an intent to minimize the amount of the tin catalyst used in the polymerization. As a result, it has been found that, in order to obtain the lactic acid-glycolic acid-copolymer having the specific range of properties in this invention, the amount of stannous octoate used as the catalyst is required at least 0.005 wt. % based on the sum of the lactide and the glycolide, but can be lowered to 0.015 wt. % or less. It has also been found that the copolymer obtained by this invented method contains substantially no endotoxin.

The lactide has a slower rate of polymerization than that of the glycolide. Accordingly in the copolymerization of the lactide and the glycolide to obtain a lactic acid-glycolic acid-copolymer having a relatively high content of the lactic acid unit, it has been thought that a larger amount of the stannous octoate catalyst is required as compared with homopolymerization of the glycolide.

However, it has been unexpectedly found that the copolymerization conducted within a specific range of temperature can remarkably reduce the conventional amount of stannous octoate catalyst in a usual polymerization time without causing decrease in desired polymerization degree and variation of ingredient proportion on the resultant copolymer.

DETAILED DESCRIPTION OF THE INVENTION

The raw material lactide can be prepared by a known process, for example, the process disclosed in the above Japanese Laid-Open Patent No. 64824/1987. The raw material glycolide can also be prepared by a known process, for example, the process described in US Patent No. 2668162. The proportion of these materials in charge is 40–50 mol % of glycolide to 50–60 mol % of lactide.

Stannous octoate used as the catalyst in this invention is preferably prepared prior to use by distilling the commercially available grade under vacuum of $10^{-3}$ mmHg. The amount of stannous octoate used is 0.005–0.015 wt. % based on the sum of raw materials, the lactide and the glycolide. When the amount of the catalyst is less than 0.005 wt. %, the polymerization degree does not increase even though the reaction temperature is raised. When the amount is more than 0.015 wt. %, tin content in the polymer is unfavorably increased and the polymerization degree of resultant polymer is also lowered inversely by conducting the polymerization in the temperature range specified in this invention. The generally preferred amount of stannous octoate used is in the range of 0.008–0.012 wt. %.

In the process of this invention, the polymerization must be carried out in the temperature range of 200°–230° C.

When the temperature is lower than 200° C., it takes a long period of time for the polymerization and a relatively large amount of unreacted monomers is also remained by using stannous octoate in the specified range. Therefore, it is required to remove the residual monomers after terminating the reaction by such methods as reprecipitation; molar proportion of the ingredients in the copolymer obtained is also dependent upon the variation of polymerization conditions and always unstable; and the copolymer having the desired properties can not always be obtained.

Deleterious endotoxin existing in the reaction system is decomposed within a shorter period of time at higher temperatures and its biological activity is eliminated. However, if the reaction is conducted at a temperature below 170° C., it is difficult to effectively reduce the content of endotoxin within the polymerization time.

On the other hand, if the reaction is conducted at a temperature above 230° C., it results in depolymerization and severe coloring of the resultant copolymer and is hence unsuitable for the process of this invention. The preferred range of the temperature is 215°–225° C. and the temperature is properly determined on the basis of the amount of catalyst.

The polymerization regulator is required also in the process of this invention. Typical examples of the regulator include alcohols such as lauryl alcohol, α-hydroxy lower fatty acids such as dl-lactic acid and glycolic acid, and water. dl-Lactic acid and glycolic acid are preferably used. When lactic acid is employed, the polymerization degree of the copolymer is apt to vary depending upon the moisture content of lactic acid used because of a strongly hygroscopic property of the acid. Therefore it is more preferred to employ a commercially available grade of 90% dl-lactic acid which has a constant moisture content. The amount for use is in the range of 0.25–0.50 wt. % based on total weight of the monomers and properly selected within the range according to the desired properties of the polymer to be obtained, amount of the catalyst and the polymerization temperature.

In the preparation process of this invention, the copolymer having desired properties can be obtained in a relatively short period of time as compared with usual processes. For example, a copolymer is prepared which contains about 55 mol % of the dllactic acid unit and about 45 mol % of the glycolic acid unit and has such physical properties as an inherent viscosity of about 0.5 in a chloroform solution. In this case, reaction time of about 2.0–2.5 hours is sufficient when the polymerization is conducted at a temperature of about 220° C. by using 0.01–0.015 wt. % of stannous octoate.

Examples will hereinafter be illustrated. The properties of the copolymers were measured by the procedures described below.

Weight average molecular weight

Weight average molecular weight of the copolymer was measured by gel permeation chromatography in a 0.1 wt. % chloroform solution. The molecular weight was obtained on the basis of polystyrene standard.

Inherent viscosity

Chloroform was used as solvent. Measurement was carried out at 25°±1° C. in a 0.5 g/dl solution. Inherent viscosity was calculated from the following equation.

$$\eta_{inh} = l_n \frac{T_1/T_0}{C}$$

$T_0$ = reference measuring time
$T_1$ = measuring time
$C$ = concentration of solution (0.5)

Composition of copolymer

A 1% solution of the copolymer is deuterated chloroform was added with a small amount of TMS and $^1$H-NMR spectrm was measured. Mole fraction of glycolic acid and lactic acid was calculated from peak intensities of methylene hydrogen in the glycolic acid unit and methyl hydrogen in the lactic acid unit.

Content of tin metal

The copolymer was decomposed with a mixture of sulfuric acid and nitric acid. Tin content was measured by absorptiometry.

Endotoxin content

The copolymer was dissolved in endotoxin free dimethyl-sulfoxide, diluted 10 times with distilled water and centrifuged. The resultant supernatant liquid was estimated by injection into a rabbit in an amount of 1 ml/kg or by LAL test.

The LAL (Limulus Amberbocyte Lysate) test means the following method.

LAL is respectively added to a sample solution and an aqueous solution having a known concentration of endotoxin. The resulting mixtures are reacted at 37° C. for 30 minutes, added with azo coloring matter to develop color and endotoxin content in the sample is measured by absorbance at 545 nm.

EXAMPLES 1-6 AND COMPARATIVE EXAMPLES 1-5

A thick-walled cylindrical stainless steel polymerization vessel equipped with a stirrer was charged with dl-lactide having a melting point of 124°-125° C. and glycolide having a melting point of 83.5-84.5° C. in amounts illustrated in Table 1. The mixture was then added with stannous octoate and polymerization regulator in amounts illustrated in Table 1, deaired for 2 hours under vacuum of 1-5 mmHg abs. and replaced with nitrogen. The resulting mixture was polymerized under the temperature and time conditions illustrated in Table 1 by heating in a mantle heater in a nitrogen atmosphere.

The physical properties of resultant copolymer is illustrated in Table 2.

Weight average molecular weight of the copolymer obtained in Example 1 was 65000. Rabbit fever test of the copolymer obtained in Example 2 resulted in no fever of the rabbit. The amount of endotoxin determined by LAL test was 0.3 pg/ml. The value was remarkably smaller than the value of 173 pg/ml which was regarded as $PD_{50}$ (minimum amount to cause fever in 50% of rabbits).

The merit of the process in this invention is clearly illustrated in the above examples.

The dl-lactic acid-glycolic acid-copolymer containing 50-60 mol % of the dl-lactic acid unit and 40-50 mol % of the glycolic acid unit and having an inherent viscosity of 0.4-0.6 measured in chloroform and a tin metal content of 50 ppm or less can be prepared in a shorter period of time than conventional processes.

In addition, when the reaction is carried out at the temperatures of this invention, the noxious endotoxin existing in the reaction system is effectively decomposed within the polymerization time. Therefore, substantially no endotoxin is contained in the resulting copolymer.

As a result, the dl-lactic acid-glycolic acid-copolymer having a high level of safety can be prepared more efficiently than conventional manufacturing processes, thereby providing a great contribution to the industry.

TABLE 1

|  | dl-Lactide (mole) | Glycolide (mole) | Stannous octoate (wt. %) | dl-lactic acid (wt. %) | Lauryl alcohol (wt. %) | Temperature (°C.) | Time (hr) |
| --- | --- | --- | --- | --- | --- | --- | --- |
| Example |  |  |  |  |  |  |  |
| 1 | 6.91 | 6.21 | 0.01 | 0.35 | 0 | 220 | 2.5 |
| 2 | 13.86 | 12.46 | 0.01 | 0.40 | 0 | 220 | 2.0 |
| 3 | 13.87 | 12.47 | 0.015 | 0.35 | 0 | 200 | 2.0 |
| 4 | 6.91 | 6.21 | 0.005 | 0.50 | 0 | 220 | 3.5 |
| 5 | 6.92 | 6.21 | 0.01 | 0.35 | 0 | 230 | 1.5 |
| 6 | 6.92 | 6.21 | 0.01 | 0 | 0.35 | 220 | 2.5 |
| Comparative Example |  |  |  |  |  |  |  |
| 1 | 6.92 | 6.21 | 0.003 | 0.35 | 0 | 220 | 3.5 |
| 2 | 6.91 | 6.21 | 0.01 | 0.10 | 0 | 180 | 3.5 |
| 3 | 6.92 | 6.22 | 0.01 | 0.35 | 0 | 250 | 2.5 |
| 4 | 6.92 | 6.21 | 0.02 | 0.35 | 0 | 220 | 2.5 |
| 5 | 6.50 | 6.50 | 0.20 | 0.73 | 0 | 160 | 6.0 |

TABLE 2

|  | Inherent viscosity (dl/g) | Copolymer composition L/G | Tin content (ppm) | Color |
| --- | --- | --- | --- | --- |
| Example 1 | 0.51 | 54/46 | 27 | pale yellow |
| 2 | 0.49 | 52/48 | 33 | colorless |
| 3 | 0.50 | 53/47 | 44 | pale yellow |
| 4 | 0.40 | 55/45 | 14 | colorless |
| 5 | 0.50 | 53/47 | 30 | pale yellow |
| 6 | 0.53 | 53/47 | 29 | colorless |
| Comparative |  |  |  |  |
| Example 1 | 0.28 | 38/62 | 10 | colorless |
| 2 | 0.32 | 40/60 | 29 | colorless |
| 3 | 0.35 | 50/50 | 30 | brown |
| 4 | 0.34 | 51/49 | 59 | brown |
| 5 | 0.26 | 43/57 | 591 | colorless |

(Note) L/G: Mole proportion of lactic acid unit to glycolic acid unit in copolymer

What is claimed is:

1. In a process for the copolymerization of a lactide and a glycolide to prepare a dl-lactic acid-glycolic acid-copolymer containing 50-60 mol % of a lactic acid unit and 40-50 mol % of a glycolic acid unit and having an inherent viscosity of 0.4-0.6 in chloroform, the improvement which comprises conducting the copolymerization in the presence of a polymerization regulator at a temperature of 200°-230° C. by using stannous octoate as a catalyst in an amount of 0.005-0.015 wt. % based on the sum of the lactide and the glycolide.

2. A process of claim 1 wherein said polymerization regulator is a α-hydroxy lower fatty acid.

3. A process for the preparation of the dl-lactic acid-glycolic acid-copolymer of claim 2 wherein said α-hydroxy lower fatty acid is dl-lactic acid containing water and the amount therefor is 0.25-0.50 wt. % based on the sum of the lactide and the glycolide.

* * * * *